United States Patent [19]

Voorhoeve

[11] Patent Number: 4,542,006

[45] Date of Patent: Sep. 17, 1985

[54] CATALYTIC PROCESS FOR THE PRODUCTION OF UREA AND AMMONIUM CYANATE

[75] Inventor: Rudolf J. H. Voorhoeve, Summit, N.J.

[73] Assignee: AT&T Bell Laboratories, Murray Hill, N.J.

[21] Appl. No.: 316,690

[22] Filed: Oct. 30, 1981

Related U.S. Application Data

[63] Continuation of Ser. No. 217,562, Dec. 17, 1980, abandoned, which is a continuation of Ser. No. 776,787, Mar. 11, 1977, abandoned.

[51] Int. Cl.$^4$ ............................ C01C 3/00; C01C 3/14
[52] U.S. Cl. ........................................ 423/365; 564/63
[58] Field of Search ..................... 423/352, 239, 365; 564/63

[56] References Cited

U.S. PATENT DOCUMENTS

| | | | |
|---|---|---|---|
| 1,083,703 | 1/1914 | Rothe | 423/352 |
| 1,487,647 | 3/1924 | Fauser | 423/235 |
| 3,425,803 | 2/1969 | Romeo | 423/239 |

FOREIGN PATENT DOCUMENTS 371210  11/1973  U.S.S.R. .

OTHER PUBLICATIONS

Mellor, Treatise on Inorganic and Theoretical Chemistry, vol. VIII (1928), p. 161.

Primary Examiner—John Doll
Assistant Examiner—Wayne A. Langel
Attorney, Agent, or Firm—Bruce S. Schneider

[57] ABSTRACT

A catalytic process has been found to produce urea or its equivalent, $NH_4NCO$, under relatively mild pressure and temperature conditions. This process entails flowing a gas mixture containing $NO_x$, CO, and a source of hydrogen such as $H_2$ or $H_2C$ over a hydrogenation catalyst such as platinum. Yields of urea above 90 percent based on $NO_x$ conversion are obtainable.

6 Claims, 7 Drawing Figures

CATALYTIC PROCESS FOR THE PRODUCTION OF UREA AND AMMONIUM CYANATE

This is a continuation of application Ser. No. 217,562 filed Dec. 17, 1980, abandoned, which is a continuation of Ser. No. 776,787 filed Mar. 11, 1977, abandoned.

BACKGROUND OF THE INVENTION

1. Field of the Invention

The invention is related to the production of urea or its equivalent such as ammonium cyanate. More particularly, the invention relates to a catalytic process for the production of these compounds.

2. Description of the Prior Art

Urea or its equivalent, i.e., ammonium cyanate, is used for many economically significant applications. For example, urea is used as a main constituent of fertilizers, as a monomer in the production of plastics, and as an ingredient in animal feed. Large quantities of urea, on the order of 4,000,000 tons/year or more in the United States alone, are synthesized commercially by contacting $CO_2$ and $NH_3$ under high pressure, typically 200 to 400 atm., and at temperatures between 140 to 210 degrees C. to form ammonium carbamate, which is then decomposed into urea and water. The high pressures necessitate the use of expensive, sophisticated equipment. Further the low conversion efficiencies usually obtained in this commercial process, e.g., about 50%, require the recycling of unreacted $NH_3$ and $CO_2$. Thus, production of smaller quantities by this high-pressure process is not fiscally acceptable. Even if large quantities are desired, the initial capital investment is an obstacle. Since the commercial production of $NH_3$, a reactant in the process, also involves a high-pressure method which is only economical on a scale of approximately 500,000 tons/year, the monetary and quantity limitations inherent in the commercial urea manufacturing process are further compounded.

Certain situations, however, are most suitable for small-quantity, low-investment techniques. For example, the need for only a relatively small capital investment would facilitate production of urea for fertilizer in a low-technology agrarian country. Similarly, the on-site production of urea from waste by-products of another process is a desirable process usually involving relatively small scales. Such a recovery process is often economically advantageous if a sufficiently high-conversion efficiency from reactant by-products, to salable products is obtainable. These two specific situations and many analogous ones illustrate two important factors. First, techniques involving relatively mild-pressure conditions are important in reducing the associated initial investment and technical complexities. Second, the possibilities of increased efficiency in the utilization of raw materials offered by a high-yield method of making urea from by-products is significant. Thus a relatively mild-pressure, high-efficiency process of making urea is beneficial in many circumstances.

SUMMARY OF THE INVENTION

It has been found that when a gaseous mixture of $NO_x$ where x is 1 or 2, carbon monoxide and a source of hydrogen, such as $H_2O$ or $H_2$, is passed over a hydrogenation catalyst, such as platinum or rhodium, urea is obtained if the product is condensed at temperatures above 60 degrees C. and ammonium cyanate, $NH_4OCN$, is obtained for condensation below 60 degrees C. Yields of up to 100 percent (based on the conversion of the $NO_x$ to urea or $NH_4OCN$) are possible. Other catalysts such as monel give lower yields, e.g., above 30 percent but are still useful. Such yields are obtained at atmospheric pressure and at temperatures between about 200 and 600 degrees C.

The process gives advantageous conversion to urea or $NH_4OCN$ when the $NO_x$ concentration is as low as 200 ppm. or as high as 5%. Thus, the method is adaptable for using the $NO_x$ by-products of other manufacturing operations. This is particularly significant since normally nitrogen oxides in low concentrations have a negative manufacturing cost, e.g., there is a significant expense in converting $NO_x$ into other relatively valueless non-pollutants to meet the requirements of federal environmental statutes. The inventive process in essence has the potential for transforming a manufacturing expense into a manufacturing asset. This transmogrification is associated with a reasonably small capital investment resulting from the relatively mild reaction conditions. The attractiveness of the process is further enhanced by the high-conversion efficiencies which are achievable.

DETAILED DESCRIPTION

Figure 1:
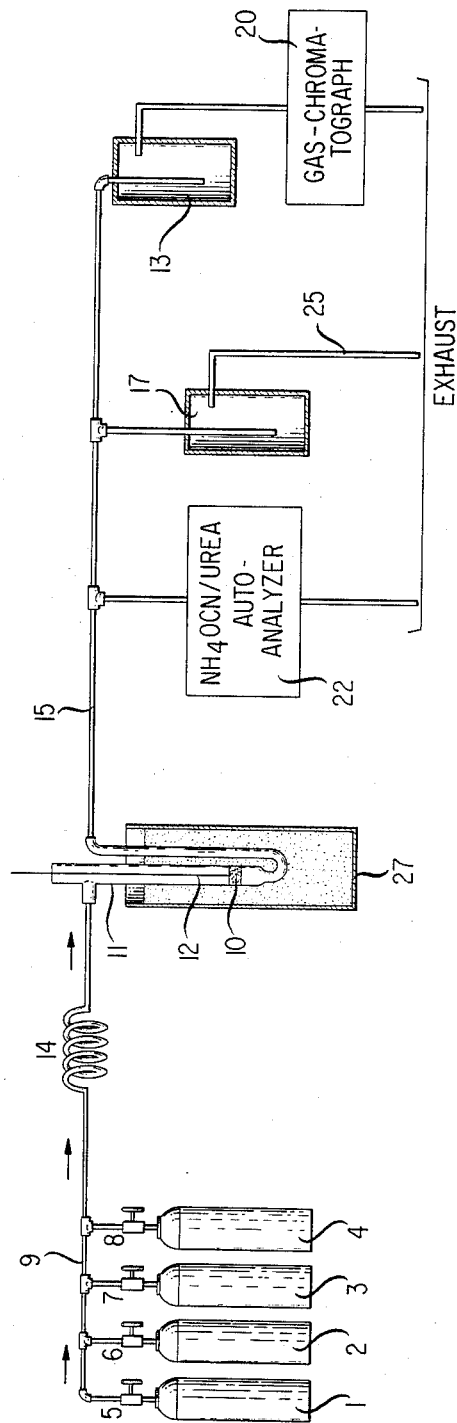
FIG. 1 is a schematic diagram of an apparatus suitable for the practice of the invention.

The preferred embodiment of the invention can best be described by individually detailing the steps in the synthesis process by reference to FIG. 1.

Cylinders of the reactant gases (1, 2, and 3 in FIG. 1) and a cylinder of an inert carrier gas 4, is attached through individual flow controllers, 5, 6, 7 and 8, to a manifold 9. The reactant gases are a nitrogen oxide, i.e., NO or $NO_2$ or a combination of NO and $NO_2$, carbon monoxide, and a third material which provides a source of hydrogen. Molecular hydrogen and water are exemplary of the materials suitable as hydrogen sources. In the latter case, since the process involves a gas phase reaction, the water is added by techniques such as passing the reactant gases through a water bubbler. Indeed, if the other reactants have a sufficiently high water impurity content no further addition is necessary. The particular material used as the inert gas is not critical. Typically, in laboratory preparation, helium is used because of its availability and because it facilitates analysis of reaction products. However, other inert gases such as $N_2$ are also acceptable.

The catalyst 10 is inserted in the reaction vessel 11, and a thermocouple 12, or other temperature monitoring means placed near the catalyst. The catalyst used is a hydrogenation catalyst. For example, catalysts such as rhodium, platinum and palladium, are suitable. Other specific hydrogenation catalysts such as monel are also useful. The physical form of the catalyst is not critical. Conventional forms such as small metal particles or a supported catalyst are useful. The yield of urea or urea equivalent i.e., $NH_4OCN$, depends on the reaction conditions and the particular catalyst used. It is desirable for many uses to select the conditions and the catalyst to yield conversions of $NO_x$ to urea or $NH_4OCN$ of greater than 30 percent. Preferably for small-scale commercial applications conversions greater than 70 percent are advantageous.

After the reactants and catalysts are positioned, the apparatus is sealed and the entire system is purged with the inert gas. Then, if desired, the catalyst is cleaned by running $H_2$ over the catalyst which is heated to between 200 and 600 degrees C., preferably between 300 and 500 degrees C. for 1 to 24 hours. For this purpose, $H_2$ is introduced in the system either in pure form or diluted with an inert gas in a ratio of inert gas to $H_2$ of between 0 and 50. This cleaning removes oxygen from the catalyst surface and generally makes the catalyst more active.

To start the reaction process, $NO_x$, CO, the hydrogen source e.g., $H_2$, and an inert gas are bled through their respective flow controllers into the manifold 9, and are directed through mixing coil 14 to insure homogeneity. Exemplary of the concentration of reactants in the gas flow is an $NO_x$ partial pressure of $2 \times 10^{-4}$ atm to 0.05 atm, preferably $2 \times 10^{-3}$ atm to 0.02 atm, a $CO/NO_x$ ratio of between 0.5 and 10, preferably between 1 and 4 and a $H_2/NO_x$ ratio of between 1 and 10, preferably between 1 and 2. The remainder of the gas flow is composed of inert gas, i.e., gas which does not interfere with the desired reaction. Suitable pressures for the total gas flow are between about $\frac{1}{2}$ and 5 atm, preferably between $\frac{3}{4}$ and $1\frac{1}{2}$ atm. Within these limitations of reactant concentration total gas flow and pressure, situations are emcompassed where no inert gas is used and the system operates at a partial vacuum. Such situations are within the ambit of the invention. However, it is generally most convenient to work at pressures in the range of 1 atm which usually necessitates the addition of some inert gas. The gas mixture is passed over the catalyst which is heated to a temperature between about 200 and 600 degrees C., preferably between 300 and 500 degrees C. The gas flow rate is regulated to allow sufficient time for a substantial portion of the reactants to react and yet provide a commercially viable throughput time. Generally, for typical catalysts, flow rates between about 1,000 and 100,000 ml/h per $m^2$ are acceptable. (The $m^2$ refers to the the total surface area of the catalyst accessible to the reactant gas flow.)

The reacted gas passes out of the reactor into tube 15 and the $NH_4OCN$ is frozen out of the gas flow by passing through a trap 17, which is kept at a temperature between 0 degree C. and 120 degrees C. Ammonium cyanate is stable in the gas phase. However, when condensed, it spontaneously converts to urea at temperatures above 60 degrees C. Urea decomposes in the solid state at 120 degrees C. Therefore if the reacted gases are frozen below 60 degrees C. $NH_4OCN$ is the solid obtained. If the gases are condensed between 60 degrees C. and 120 degrees C., urea is obtained. Condensation above 120 degrees C. is not recommended. The remaining gases are then vented through tube 25.

The ultimate yield obtained depends on the particular reaction conditions used. In each specific situation a controlled sample is used to fix the desired optimum conditions. The following examples demonstrate the effect of various parameters and the results obtainable by the practice of the invention.

Examples 1 through 4 show the effect of temperature on yield for various catalysts. Each example was done with a total gas pressure of 1 atm.

EXAMPLE 1

The apparatus shown in FIG. 1 including, for the purpose of analysis, a gas chromatograph 20, to measure the concentration of $NO_x$ and $N_2$ in the exhaust gas and a Modified Technicon Colorimetric Auto-Analyzer 22, to measure the concentration of $NH_4OCN$, was used. The modification of the analyzer was necessary to prevent clogging of the apparatus with urea or $NH_4OCN$. The modification consisted of installing an absorber which forced the hot gases through a silver nozzle followed by condensation and dissolution of the cyanate component on a surface which is continually flushed with an alcoholic solution. The solution is heated to between 60 and 90 degrees C. to effect total conversion to urea. The urea solution is then analyzed using the carbamido-diacetyl reaction. (See *J. Biochemistry* 33, 902 (1939).)

Figure 2:
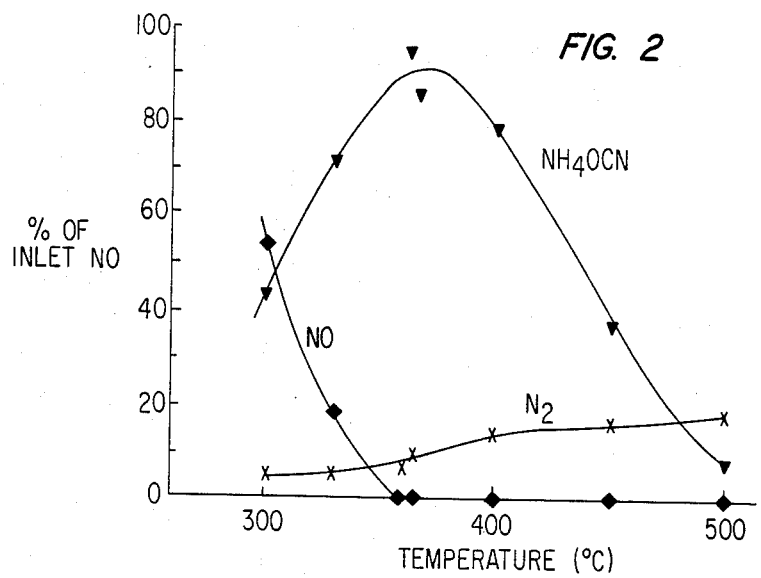
FIGS. 2–7 show conversion efficiencies under various reaction conditions.

Approximately 5 grams of platinum sponge with an active surface area of 0.12 $m^2/gm$ (area available for contact with the reactants) was put into the reaction vessel. A gas mixture of 0.3 percent NO, 0.5 percent $H_2$, 5.0 percent CO and the remainder He was flowed at 115 cc/min over the catalyst (total pressure 1 atm). Measurement of urea ($NH_4OCN$) production for various temperatures of the catalyst in the range of 300 to 500 degrees C. was made. (The catalyst was heated by a fluidized sand bed with a heating coil, 27.) A sample of the reactor effluent was dried and $CO_2$ removed with an ascarite trap 13. Exhaust from the ascarite trap was analyzed on the gas chromatograph for components such as $N_2$, NO, $NO_2$ and CO. Another sample of effluent was analyzed in the auto-analyzer 22, for $NH_4OCN$ and/or urea content. The results are shown graphically in FIG. 2.

EXAMPLE 2

Figure 3:
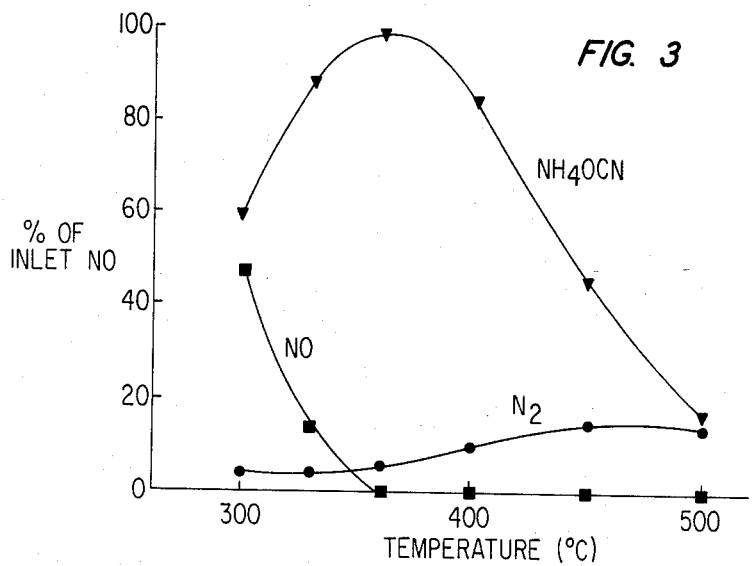

The catalyst of Example 1 was reduced (cleaned) by running a 2 percent $H_2$ in He mixture over the platinum sponge for 8 hours at 480 degrees C. and then for 3 hours at 500 degrees C. The data obtained under the same reaction conditions as in Example 1 is shown in FIG. 3.

A comparison of these two FIGS. shows the improved effect generally associated with cleaning the catalyst.

EXAMPLE 3

Figure 4:
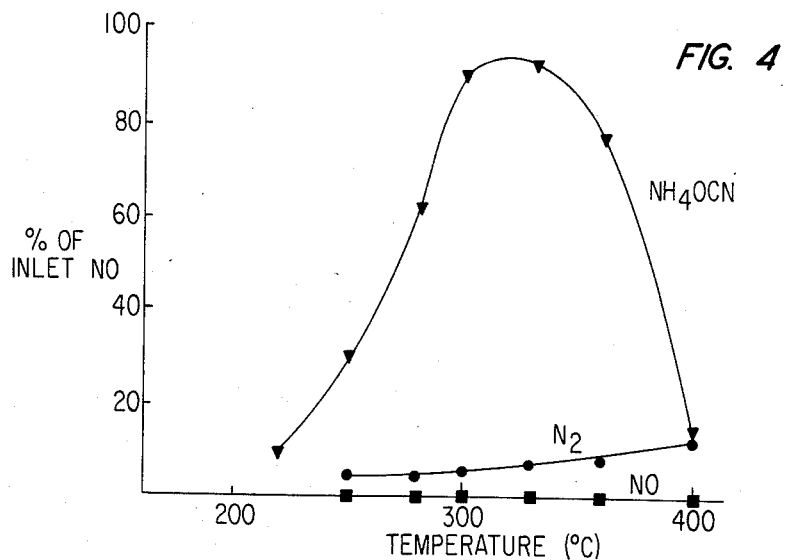

Approximately 1.5 grams of rhodium sponge with an active surface area of 1.69 $m^2/gm$ was put into the reaction chamber. Pure $H_2$ was flowed over the catalyst at 100 cc/min. The catalyst was heated to 500 degrees C. and maintained at this temperature for $1\frac{3}{4}$ hours. The catalyst temperature was then reduced to room temperature and the gas flow was changed from pure $H_2$ to pure He for overnight storage. A mixture of 0.31 percent NO, 0.5 percent $H_2$, 5.0 percent CO, and the balance He (total pressure 1 atm) was flowed at a rate of 230 cc/min. over the rhodium as it was heated to 360 degrees C. Product analysis was then done at various catalyst temperatures and the result is shown in FIG. 4.

EXAMPLE 4

Figure 5:
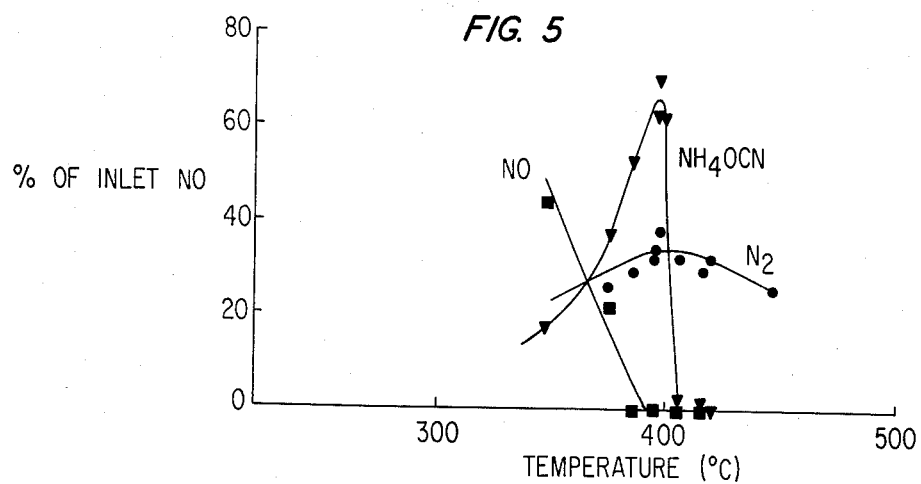

Approximately 4 grams of monel metal filings (active surface area 0.12 $m^2/gm$) was placed in the reactor and heated to 450 degrees C. under a 2 percent $H_2/He$ flow of 100 cc/min. The cleaning process was continued overnight. The catalyst temperature was then lowered to 200 degrees C. and the gas flow was changed to pure $H_2$ at 100 cc/min. The temperature was then increased to 450 degrees C. for $4\frac{1}{4}$ hours. Various runs were made and the system was kept under He for a number of days. Then a gas flow of 0.3 percent NO, 0.5 percent $H_2$, 5.0 percent CO and the remainder He was introduced at a flow rate of 125 cc/min (total pressure 1 atm). Yields were measured at various catalyst temperatures over an extended period. The catalyst was kept under pure He when measurements were not being taken. The results are shown in FIG. 5.

As can be seen from FIGS. 2 to 5 conversions of NO to $NH_4OCN$ closely approaching 100% were possible.

The following example demonstrates a typical effect of flow rate on yield at various temperatures.

EXAMPLE 5

Figure 6:
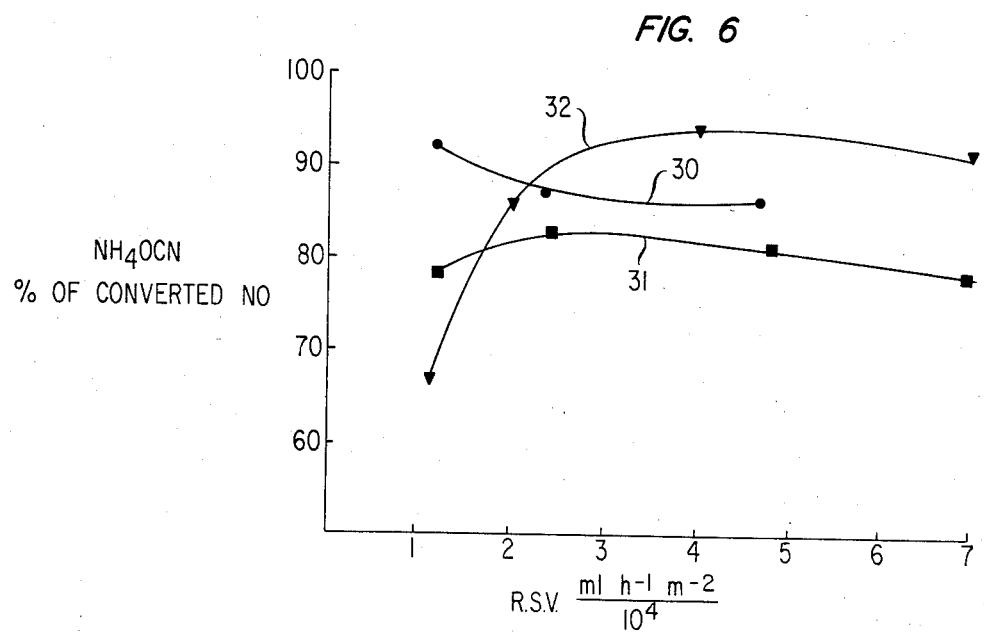

The catalyst used in Example 1 was again reduced at 500 degrees C. under 2 percent $H_2$ in He (2 hours). Yields at 360 and 410 degrees C. for various flow rates of a 0.3 percent NO, 0.5 percent $H_2$, 5.0 percent CO, and the remainder He (total gas pressure 1 atm) mixture was measured. Line 30 of FIG. 6 indicates the results at the lower temperature and line 31 at the higher.

A different sample of approximately 5 grams of platinum sponge (active surface area 0.12 $m^2/gm$) was reduced overnight at 500 degrees C. under a 2 percent $H_2$/He flow. The catalyst temperature was adjusted to 430 degrees C. and a gas mixture of 0.33 percent NO, 0.5 percent $H_2$, 5.0 percent CO and the remainder He (total pressure 1 atm) was introduced at a flow rate of 700 ml/min. This flow rate was varied by partial venting the gas flow before the gas mixture reached the reactor. The yields of $NH_4CNO$ for the different flow rates at 430 degrees C. are indicated by line 32 in FIG. 6. (Flow rates are shown as F/S where F is gas volume in ml per hour and S is the surface area of the catalyst sample accessible to the reactant gas flow.)

The following example illustrates the effect of reactant proportions on the reaction yield.

EXAMPLE 6

Approximately 5 grams of platinum sponge (active surface area 0.12 $m^2/gm$) was loaded in the reactor. The catalyst temperature was raised to 450 degrees C. and 2 percent $H_2$/He was flowed at a rate of 60 cc/min. through the system overnight. The temperature was then lowered to 404 degrees C. and a gas mixture containing 0.3 percent NO, 5.0 percent CO, 0.3 percent $H_2$ and the balance He (total gas pressure 1 atm) was followed at the rate of 400 cc/min. through the system. The CO concentration was varied (He concentration was also varied to compensate) and the yield of $NH_4OCN$ measured. The following results were obtained.

| CO conc. Percent | Percent Conversion NO to $NH_4OCN$ |
| --- | --- |
| 5.0 | 100 (82*) |
| 2.0 | 100 (72*) |
| 1.75 | 69.5* |
| 1.25 | 63.0* |
| 0.89 | 45.0* |
| 0.45 | 37.5 (34.5*) |

*Reading taken on second day of experiment after catalyst was kept in He atmosphere over a 3 day period at room temperature.

The flow was then changed to a 2 percent $H_2$/He mixture (flow rate 60 cc./min.) and the catalyst was reduced overnight at 450 degrees C. The catalyst temperature was lowered to 420 degrees C. and various reaction mixtures were flowed (400 cc./min.) through the system (total pressure of any given mixture was 1 atm). The composition of the reactant gas mixture (remainder not shown was He) and the $NH_4OCN$ yield is shown in the following tables.

| Effect of NO and $H_2$ Conc. | | | |
| --- | --- | --- | --- |
| % NO | % CO | % $H_2$ | % Conversion NO to $NH_4OCN$ |
| 0.6 | 5.0 | 0.6 | 62.0 |
| 1.2 | 5.0 | 1.2 | 63.0 |
| 1.2 | 5.0 | 3.2 | 30.5 |
| 2.0 | 5.0 | 2.0 | 53.5 |
| 2.0 | 5.0 | 3.0 | 53.5 |

| Effect of $H_2O$ | | | | |
| --- | --- | --- | --- | --- |
| % NO | % CO | % $H_2$ | % $H_2O$ | % Conversion |
| 0.6 | 5.0 | 0.6 | 0.0 | 62.0 |
| 0.6 | 5.0 | 0.6 | 4.3 | 77.5 |
| 0.6 | 5.0 | 0.0 | 4.3 | 69.0 |
| 0.6 | 2.0 | 0.6 | 4.3 | 72.5 |
| 0.3 | 2.0 | 0.5 | 0.0 | 62.0 |
| 0.3 | 2.0 | 0.5 | 4.3 | 60.5 |
| 2.0 | 5.0 | 2.0 | 4.5 | 61.0 |

The above tables show that conversion efficiency was insensitive to $H_2$/NO ratio near stoichiometric proportions but that efficiency was reduced significantly when the $H_2$/NO ratio was increased above approximately 1.5. The table further shows that $H_2O$ was effectively used as a source of hydrogen.

The following example illustrates the effect of $O_2$ on the reaction yield. It should be noted that when $O_2$ was introduced NO was converted to $NO_2$.

EXAMPLE 7

Figure 7:
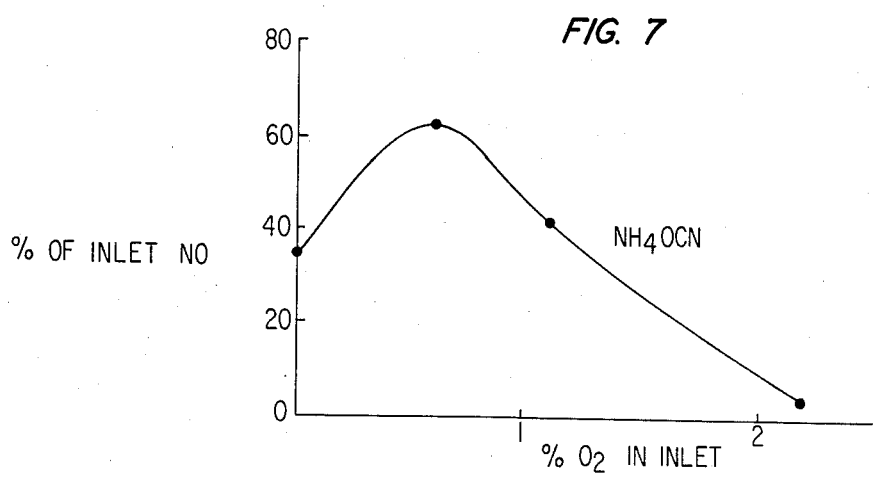

Approximately 5 grams of sponge platinum in a reduced state was raised to 500 degrees C. and a gas flow of 0.33 percent NO, 0.5 percent $H_2$, 5.0 percent CO, (remainder He, total gas pressure 1 atm) was flowed through the system at a rate of 14 l/h. Various percentages of $O_2$ were introduced and conversion efficiencies measured. The results are shown in FIG. 7.

What is claimed is:

1. The process comprising converting a mixture of gases, said mixture of gases comprising (1) an oxide of the composition $NO_x$ where x is 1 or 2, (2) carbon monoxide and (3) a source of hydrogen, to a compound of the formula $N_2H_4CO$ in the presence of a hydrogenation catalyst and collecting said compound.

2. The process of claim 1 wherein said hydrogenation catalyst is chosen from the group consisting of platinum, rhodium, palladium, and monel.

3. The process of claim 1 wherein said process is done at a temperature in the range of about 200 to 600 degrees C.

4. The process of claim 1 wherein said source of hydrogen is selected from the group consisting of molecular hydrogen and water.

5. The process of claim 1 wherein said process is done at a temperature in the range of about 300 to 500 degrees C.

6. The process of claim 1 wherein said mixture of gases includes oxygen.

* * * * *

UNITED STATES PATENT AND TRADEMARK OFFICE
CERTIFICATE OF CORRECTION

PATENT NO. : 4,542,006

DATED : September 17, 1985

INVENTOR(S) : Rudolf J. H. Voorhoeve

It is certified that error appears in the above-identified patent and that said Letters Patent is hereby corrected as shown below:

Column 5, lines 45-46, "followed" should read --flowed--.

Signed and Sealed this

Eighth Day of April 1986

[SEAL]

Attest:

DONALD J. QUIGG

Attesting Officer

Commissioner of Patents and Trademarks